(12) United States Patent
Golan (10) Patent No.: US 11,206,802 B2
(45) Date of Patent: Dec. 28, 2021

(54) METHODS OF CULTIVATING ECTOMYCORRHIZAL FUNGI

(71) Applicant: Ezekiel Golan, Vancouver (CA)

(72) Inventor: Ezekiel Golan, Vancouver (CA)

( * ) Notice: Subject to any disclaimer, the term of this patent is extended or adjusted under 35 U.S.C. 154(b) by 325 days.

(21) Appl. No.: 16/060,031

(22) PCT Filed: Dec. 7, 2016

(86) PCT No.: PCT/IL2016/051310
§ 371 (c)(1),
(2) Date: Jun. 7, 2018

(87) PCT Pub. No.: WO2017/098509
PCT Pub. Date: Jun. 15, 2017

(65) Prior Publication Data
US 2018/0359982 A1 Dec. 20, 2018

Related U.S. Application Data

(60) Provisional application No. 62/263,796, filed on Dec. 7, 2015.

(51) Int. Cl.
*A01G 18/10* (2018.01)
*A01H 17/00* (2006.01)
*A01G 18/64* (2018.01)

(52) U.S. Cl.
CPC .............. *A01H 17/00* (2013.01); *A01G 18/10* (2018.02); *A01G 18/64* (2018.02)

(58) Field of Classification Search
CPC ..................................................... A01G 18/10
See application file for complete search history.

(56) References Cited

U.S. PATENT DOCUMENTS

2003/0203474 A1  10/2003  Wang
2004/0000090 A1*  1/2004  Miller .................... A01G 18/00
                                                                47/1.1
2005/0132431 A1   6/2005  Coughlan et al.

FOREIGN PATENT DOCUMENTS

WO  WO 2012/110673  8/2012
WO  WO 2014/102784  7/2014
WO  WO 2017/098509  6/2017

OTHER PUBLICATIONS

Hertel, et al. (Biotropica 43.4 (2011): 401-404). (Year: 2011).*
Stevens, et al. (Tree physiology 38.6 (2018): 877-894). (Year: 2018).*
Suryanarayanan, et al. (Fungal Divers 8 (2001): 155-161). (Year: 2001).*
Hertel et al. (Biotropica 43(4): 401-404 2011). (Year: 2011).*
International Preliminary Report on Patentability dated Jun. 21, 2018 From the International Bureau of WIPO Re. Application No. PCT/IL2016/051310. (7 Pages).
International Search Report and the Written Opinion dated Mar. 19, 2017 From the International Searching Authority Re. Application No. PCT/IL2016/051310. (10 Pages).
Abdou et al. "Vegetative Propagation Trial of Prosopis Africana (Guill. et Perr.) Taub. by Air Layering Under Sudano-Sahelian Climate in the South-Central Niger", Journal of Botany, 2015(Art. ID 286583): 1-6, 2015.
Arnolds "Decline of Ectomycorrhizal Fungi in Europe", Agriculture, Ecosystems and Environment, 35(2-3): 209-244, Apr. 1991.
Brennan et al. "Vegetative Propagation of Inga Feuillei From Shoot Cuttings and Air Layering", New Forests, 15(1): 37-51, Jan. 1998.
Danell et al. "Successful Cultivation of the Golden Chanterelle", Nature, 385(6614): 303, Jan. 23, 1997.
Ditengou et al. "Volatile Signalling by Sesquiterpenes From Ectomycorrhizal Fungi Reprogrammes Root Architecture", Nature Communications, 6(6279): 1-9, Feb. 23, 2015.
Duran-Casas et al. "Evaluation of Uva Camarona (Macleania Rupestris Kunth A.C. Smith) Propagation With Air Layering", Agronomia Colombiana, 31(1): 18-26, 2013.
Guerin-Laguette et al. "Lactarius Deliciosus and Pinus Radiata in New Zealand: Towards the Development of Innovative Gourmet Mushroom Orchards". Mycorrhiza, 24(7): 511-523, Published Online Mar. 28, 2014.
Habib et al. "Molecular Physiology of Tree Ectomycorrhizal Interactions", Plant Roots: The Hidden Half, Chap.39: 39-1-39-2, 2013.
Hall et al. "The Cultivation of Mycorrhizal Mushrooms—Success and Failure", Proceedings of the 5th International Conference on Mushroom Biology and Mushroom Products, Shanghai, China, 12 (Suppl.): 45-60, Apr. 2005.
Herrin et al. "The Response of Stem Girdling and Covering Material on Airlayering Propagation of Rubber Plants". 92nd Annual Meeting of the American Society for Horticultural Science, 40th Annual Congress of the Canadian Society for Horticultural Science, Montreal, Quebec, Canada, Jul. 30-Aug. 3, 1995, HortScience, 30(4): 914, #1250, Jul. 1995.
Janos et al. "Inoculation With Arbuscular Mycorrhizal Fungi Enhances Growth of Litchi Chinensis Sonn. Trees After Propagation by Air-Layering", Plant and Soil, 233(1): 85-94, Jun. 2001.
Kawai "Artificial Ectomycorrhiza Formation on Roots of Air-Layered Pinus Densiflora Saplings by Inoculation With Lyophyllum Shimeji", Mycologia, 89(2): 228-232, Mar.-Apr. 1997.
Menkis et al. "Fungal Communities in Mycorrhizal Roots of Conifer Seedlings in Forest Nurseries Under Different Cultivation Systems, Assessed by Morphotyping, Direct Sequencing and Mycelial Isolation", Mycorrhiza, 16(1): 33-41, Published Online Sep. 22, 2005.
Moreira et al. "Propagation of the Endangered Azorean Cherry Prunus Azorica Using Stem Cuttings and Air Layering", Arquipelago: Life and Marine Sciences, 26: 9-14, 2009.
Pilz et al. "Ecology and Management of Commercially Harvested Chanterelle Mushrooms", United States Department of Agriculture, USDA, Forest Service, Pacific Northwest Research Station, p. 1-83, Mar. 2003.

(Continued)

*Primary Examiner* — Charles Logsdon (57) ABSTRACT

A method of inoculating a tree with an ectomycorrhizal fungus is disclosed. The method comprises contacting at least one non-terrestrial adventitious root of the tree with the ectomycorrhizal fungus under conditions suitable for inoculation of the at least one non-terrestrial adventitious root by the ectomycorrhizal fungus. Methods of cultivating the ectomycorrhizal fungus are also disclosed as well as systems and devices for same.

15 Claims, 6 Drawing Sheets
(3 of 6 Drawing Sheet(s) Filed in Color)

(56) References Cited

OTHER PUBLICATIONS

Pyare et al. "Mechanisms of Truffle Detection by Northern Flying Squirrels", Canadian Journal of Zoology, 79(6): 1007-1015, Published Online Jun. 7, 2001.

Rewald et al. "Minirhizotron Techniques", Plant Roots: The Hidden Half, 4th Ed., Chap.42: 42-1, 42-5-42-6, 2012.

Santelices et al. "Controlled Rhizogenesis and Mycorrhization of Hazelnut (*Corylus avellana* L.) Cuttings With Black Truffle (*Tuber melanosporum* Vitt.)", Chilean Journal of Agricultural Research, 70(2): 204-212, Apr.-Jun. 2010. Abstract, p. 206, Left Col. Last Para, Figs. 1, 2.

Savoie et al. "Production of Edible Mushrooms in Forests: Trends in Development of A Mycosilviculture", Applied Microbiology and Biotechnology, 89(4): 971-979, Published Online Dec. 4, 2010.

Walters "Vegetative Reproduction by Layering Versus Sexual Reproduction in A Spruce-Fir Forest at Alpine Treeline, Medicine Bow Mountains, USA", A Thesis Submitted to the Graduate Faculty of Wake Forest University Graduate School of Arts and Sciences, Winston-Salem, North Carolina, USA, in Partial Fulfillment of the Requirements of the Degree of Master of Science, Biology, p. 1-52, Dec. 2012.

Yun et al. "Edible Ectomycorrhizal Mushrooms: Challenges and Achievements", Canadian Journal of Botany, 82(8): 1063-1073, Published Online Aug. 17, 2004.

\* cited by examiner

METHODS OF CULTIVATING ECTOMYCORRHIZAL FUNGI

RELATED APPLICATIONS

This application is a National Phase of PCT Patent Application No. PCT/IL2016/051310 having International filing date of Dec. 7, 2016, which claims the benefit of priority under 35 USC § 119(e) of U.S. Provisional Patent Application No. 62/263,796 filed on Dec. 7, 2015. The contents of the above applications are all incorporated by reference as if fully set forth herein in their entirety.

FIELD AND BACKGROUND OF THE INVENTION

The present invention, in some embodiments thereof, relates to methods of cultivating ectomycorrhizal fungi on adventitious roots of trees.

Mycorrhiza are symbiotic associations in which fungi become integrated into the physical structure of the roots of a plant. Ectomycorrhiza (EM) and endomycorrhiza are the two basic types of mycorrhizal associations. Endomycorrhizal fungi invade the living cells of the root which become filled with mycelial clusters. In a widespread form of endomycorrhiza, the microscopic appearance of intracellular hyphal clusters leads to the name of vesicular-arbuscular (VA) mycorrhiza. By contrast, the EM fungal hyphae penetrate the intracellular spaces of the epidermis and of the cortical region of the root but do not invade the living cells. The morphology of the root is altered, forming a shorter, dichotomously branching cluster with a reduced meristematic region. The external pseudoparenchymatous sheath formed by EM fungi can constitute up to 40% of the dry weight of the combined root-fungus structure. Ectomycorrhizal associations are commonly found in gymnosperms (that include pine, spruce and fir) and angiosperm species (that include oak, beech and birch).

The number of plants capable of normal development in the absence of mycorrhizal involvement is somewhat limited. The majority of plants in nature rather rely on such mycorrhizal association for their normal growth and development. For example, EM act as an extension of the colonized plant's roots, increasing the plant's absorbative surface by approximately 700%, allowing additional uptake of water and nutrients. The EM association reduces drought stress and the need for artificial fertilizer and pesticides since the plant derives several benefits from its association with EM fungi, including increased longevity of feeder roots, increased rates of nutrient absorption from soil, selective absorption of certain ions from soil, resistance to plant pathogens, increased tolerance to toxins and increased tolerance to extremes of a range of environmental parameters, such as temperature, drought and pH.

Ectomycorrhizal fungi also find advantages from EM association. Indeed, EM fungi benefit from carbohydrates, amino acids and vitamins produced by the plant. The symbiotic association between a plant and an ectomycorrhizal fungus is essential for completion of the fungal life cycle.

The study of the EM fungus *Tuber melanosporum* has increased in recent years because they are responsible for the formation of black truffles, which are a valued gastronomic product. Since the symbiosis between this fungus and a host plant is critical for black truffles development, the many attempts to grow black truffles in a sterile medium, in the absence of a host plant, remain unsuccessful. Therefore, the only way to produce black truffles known in the prior art is to harvest *T. melanosporum* associated with the roots of a plant.

To enhance the production of black truffles, terrestrial plant roots can be inoculated with *T. melanosporum* and further grown in a soil. Inoculation of roots with *T. melanosporum* is nearly always carried out with suspensions of spores or specially gathered mycorrhizal roots. Ectomycorrhizal fungal inoculum for woody plants such as pines have been produced. For example, U.S. Pat. No. 4,327,181 discloses a liquid culture of selected fungi for broadcast over forest soil. U.S. Pat. No. 5,178,642 discloses a process for production of inocula for herbaceous plants.

U.S. Pat. No. 4,749,402 describes a method for enhancing the development of mycorrhizal fungi in the root system of a plant. Particularly, this invention relates to a nutrient composition adapted for foliar fertilization of a plant to enhance the development of mycorrhiza on the root system.

Additional background art includes PCT Application WO2014/102784 and Masataka Kawai Mycologia, 89(2), 1997, pp. 228-232.

SUMMARY OF THE INVENTION

According to an aspect of some embodiments of the present invention there is provided a method of inoculating a tree with an ectomycorrhizal fungus comprising contacting at least one non-terrestrial adventitious root of the tree with the ectomycorrhizal fungus under conditions suitable for inoculation of the at least one non-terrestrial adventitious root by the ectomycorrhizal fungus, thereby inoculating the tree with the ectomycorrhizal fungus.

According to an aspect of some embodiments of the present invention there is provided a method of cultivating an ectomycorrhizal fungus on a tree, comprising growing the ectomycorrhizal fungus on at least one inoculated non-terrestrial adventitious root of the tree, thereby cultivating the ectomycorrhizal fungus on the tree.

According to an aspect of some embodiments of the present invention there is provided a tree comprising at least one non-terrestrial adventitious root, the root being inoculated by an ectomycorrhizal fungus.

According to an aspect of some embodiments of the present invention there is provided a method of monitoring the growth of an ectomycorrhizal fungus, the method comprising:

(a) growing the ectomycorrhizal fungus on at least one inoculated non-terrestrial adventitious root of the tree; and (b) analyzing the growth of the fungus, thereby monitoring the growth of the ectomycorrhizal fungus.

According to an aspect of some embodiments of the present invention there is provided a container for cultivating an ectomycorrhizal fungus on a tree, the container comprising means for hanging the container on a trunk of the tree and at least one aperture for entry of a non-terrestrial adventitious root of the tree, the at least aperture being positioned such that the non-terrestrial adventitious root is not exposed to light when cultivated in the container which is filled with soil.

According to an aspect of some embodiments of the present invention there is provided a system comprising a plurality of the containers described herein.

According to some embodiments of the invention, the method further comprises contacting the at least one non-terrestrial adventitious root of the tree with the ectomycorrhizal fungus under conditions suitable for inoculation of the at least one adventitious root by the ectomycorrhizal fungus prior to the growing.

According to some embodiments of the invention, the method further comprises generating the non-terrestrial adventitious root of the tree prior to the contacting.

According to some embodiments of the invention, the tree is at least one meter high.

According to some embodiments of the invention, the method further comprises monitoring the growing.

According to some embodiments of the invention, the monitoring is effected by analyzing levels of MiSSP7 on the at least one adventitious root.

According to some embodiments of the invention, the ectomycorrhizal fungus is an edible ectomycorrhizal fungus.

According to some embodiments of the invention, the ectomycorrhizal fungus is of a genus selected from the group consisting of *Tuber, Cantharellus, Boletus, Tricholoma, Hydnum, Lepista, Amanita, Russula, Morchella, Rhizopogon, Craterellus, Lactarius, Polyozellus, Chroogomphus, Laccaria, Albatrellus, Suillus, Amanita, Cortinarius, Gomphus, Entoloma* and *Inocybe*.

According to some embodiments of the invention, the ectomycorrhizal fungus is of a genus selected from the group consisting of *Tuber, Cantharellus, Boletus, Tricholoma, Hydnum, Lepista, Amanita, Russula, Morchella, Rhizopogon, Craterellus, Lactarius, Polyozellus, Chroogomphus, Laccaria, Albatrellus* and *Suillus*.

According to some embodiments of the invention, the ectomycorrhizal fungus is of a genus selected from the group consisting of *Tuber, Cantharellus, Boletus, Tricholoma, Hydnum, Lepista, Amanita, Russula, Morchella* and *Rhizopogon*.

According to some embodiments of the invention, the tree is of the Fagales order.

According to some embodiments of the invention, the tree is of the family selected from the group consisting of Fagaceae, Betulaceae, Juglandaceae, Salicaceae and Malvaceae.

According to some embodiments of the invention, the tree is of the species selected from the group consisting of oak (*Quercus*), chestnut (*Castanea*), beech (*Fagus*), birch (*Betula*), alder (*Alnus*), hornbeam (*Carpinus*), hazel (*Corylus*), walnut (*Juglans*), hickory (*Carya*), willow (*Salix*), poplar (*Populus*), maple (*Acer*) and linden (*Tilia*).

According to some embodiments of the invention, the contacting is effected by planting the non-terrestrial adventitious root in soil which comprises an inoculum of the ectomycorrhizal fungus, the soil being adapted for growth of the ectomycorrhizal fungus.

According to some embodiments of the invention, the contacting is effected by:

(a) planting the non-terrestrial adventitious root in soil which is adapted for growth of the ectomycorrhizal fungus; and (b) inoculating the soil with the ectomycorrhizal fungus.

According to some embodiments of the invention, the soil is deficient in at least one mineral selected from the group consisting of nitrogen, potassium, calcium, phosphorous, sulfur, magnesium and iron.

According to some embodiments of the invention, the method further comprises inoculating the soil with the ectomycorrhizal fungus prior to the contacting.

According to some embodiments of the invention, the soil naturally comprises rhizomorphs of ectomycorrhizal fungus.

According to some embodiments of the invention, the generating the non-terrestrial adventitious root comprises placing a non-terrestrial root or a branch of a tree in a soil which is adapted for growth of an adventitious root.

According to some embodiments of the invention, the soil which is adapted for growth of the adventitious root is a nutrient rich soil.

According to some embodiments of the invention, the method further comprises rinsing the soil which is adapted for adventitious root growth from the adventitious root prior to the contacting.

According to some embodiments of the invention, the growing is effected in a container.

According to some embodiments of the invention, at least a portion of the container is permeable to light so as to allow monitoring of the growth of the ectomycorrhizal fungus.

According to some embodiments of the invention, the permeable portion of the container is covered by a removable cover, the removable cover being impermeable to light so as to block light permeation in the absence of the monitoring.

According to some embodiments of the invention, the container comprises a rhizotron.

According to some embodiments of the invention, the container is elevated at least 1 meter above the ground comprising the primary roots of the tree.

According to some embodiments of the invention, the container is fixed to the tree.

According to some embodiments of the invention, the growing is effected until generation of a fruiting body from the ectomycorrhizal fungus.

According to some embodiments of the invention, the fruiting body is epigeous.

According to some embodiments of the invention, the fruiting body is hypogeous.

According to some embodiments of the invention, the method further comprises detecting the fruiting body.

According to some embodiments of the invention, the tree is at least one meter high.

According to some embodiments of the invention, the non-terrestrial adventitious root is planted in soil in a container.

According to some embodiments of the invention, the tree comprises a plurality of non-terrestrial adventitious roots wherein at least two of the non-terrestrial adventitious roots are planted in soil in separate containers.

According to some embodiments of the invention, the at least one non-terrestrial adventitious root is artificially irrigated.

According to some embodiments of the invention, the container is elevated at least 1 meter above the primary roots of the tree.

According to some embodiments of the invention, the container is attached to the tree.

According to some embodiments of the invention, at least a portion of the container is permeable to light so as to allow monitoring of the growth of the ectomycorrhizal fungus.

According to some embodiments of the invention, the permeable portion of the container is covered by a removable cover, the removable cover being impermeable to light so as to block light permeation in the absence of the monitoring.

According to some embodiments of the invention, the means for hanging the container are attached to a rim around the aperture.

According to some embodiments of the invention, the means for hanging the container is a handle extending from at least one wall of the container.

According to some embodiments of the invention, the container further comprises a handle extending from at least one wall of the container.

According to some embodiments of the invention, at least a portion of the container is permeable to light so as to allow monitoring of the growth of the ectomycorrhizal fungus.

According to some embodiments of the invention, the permeable portion of the container is covered by a removable cover, the removable cover being impermeable to light so as to block light permeation in the absence of the monitoring.

According to some embodiments of the invention, the container is fabricated from a material selected from the group consisting of wood, a textile and a ceramic.

According to some embodiments of the invention, the textile is a geotextile.

According to some embodiments of the invention, the container is fabricated from a porous material.

According to some embodiments of the invention, the container further comprises a second aperture positioned to allow drainage of water.

According to some embodiments of the invention, the containers are connected by connecting elements so as to form a chain.

According to some embodiments of the invention, the system further comprises an irrigation system.

According to some embodiments of the invention, the system further comprises a rhizotron.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D are photographs of the steps that may be carried out in order to inoculate adventitious roots with an ectomycorrhizal fungi according to embodiments of the present invention. FIG. 1A—a hole is drilled into the trunk of a live, mature tree. FIG. 1B—The hole is plugged with cotton that has been soaked in rooting hormone and antibiotics. The grommet shown is the "portal" for the adventitious roots. FIG. 1C—a container comprising soil is placed at a convenient height suspended by the grommet shown in FIG. 1D. The container is filled with soil. Test tubes may be inserted into the soil to allow a small camera to monitor root formation in a non-invasive way.

FIGS. 2A-D are photographs of the steps that may be carried out in order to inoculate adventitious roots with an ectomycorrhizal fungi according to embodiments of the present invention.

DESCRIPTION OF SPECIFIC EMBODIMENTS OF THE INVENTION

The present invention, in some embodiments thereof, relates to methods of cultivating ectomycorrhizal fungi on adventitious roots of trees.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Edible ectomycorrhizal mushrooms (EEM) comprise a specific group of edible fungal species that form symbiotic associations with their host plants. This includes about 200 common edible ectomycorrhizal mushroom species that are widely eaten in the Northern Hemisphere. A few species have well-established worldwide markets in excess of 2 billion USD, while many others are locally important.

The market of EEMs is supplied from what can be harvested from natural forests. Unfortunately, harvests of many edible mushrooms have declined over the past century, because of changes in their natural environment caused by various natural and social factors. For example, *Tuber melanosporum* harvests have fallen from around 2000 t in the 1900s to sometimes less than 100 t annually. Similarly, current matsutake production in Japan is just 5% of 1940s harvests.

The decline in the availability of EEMs, and increased demand have encouraged research into developing technologies for the cultivation of EEMs as well as methods for the sustainable productivity in natural forests. Despite numerous scientific publications and the establishment of thousands of hectares of plantations, the downward trend in EEM production continues.

The present inventors have now conceived of a novel method of cultivating ectomycorrhizal fungi such that harvesting the fruits of the fungi (e.g. truffles) will no longer disturb the terrestrial cooperative relationship between fungi and trees. Specifically, the current inventors envisage cultivating the fungi on non-terrestrial adventitious roots of a tree.

Culturing on adventitious roots is advantageous over culturing on the primary terrestrial root system since it does not put the health of the tree at risk. Furthermore, the inoculated root system remains isolated from the surroundings which have been known to discourage development of truffles (in particular, but mycorrhizae in general).

The adventitious roots are allowed to grow above ground in soil which allows the symbiotic relationship between roots and fungus to flourish. Containers comprising the soil are designed so as to allow underground growth conditions. By physically raising the height at which the fungi are cultivated, it becomes possible to monitor the growth of the fungi, such as by visualization. Furthermore, the fruits of the fungi can be harvested without scavenging amongst the forest floor and the use of harmful animals such as pigs and dogs which currently are used to sniff out the fruit becomes obsolete.

Thus, according to a first aspect of the present invention, there is provided a method of inoculating a tree with an ectomycorrhizal fungus comprising contacting at least one non-terrestrial adventitious root of the tree with the ectomycorrhizal fungus under conditions suitable for inoculation of the at least one non-terrestrial adventitious root by the ectomycorrhizal fungus, thereby inoculating the tree with the ectomycorrhizal fungus.

As used herein, the term "ectomycorrhizal fungus" refers to a fungus that grows in a symbiotic association with woody plants (e.g. trees), and does not penetrate its host's cell walls. It forms an intercellular interface, consisting of highly branched hyphae forming a latticework between epidermal and cortical root cells, known as the Hartig net. The fungus increase the plants water and nutrient uptake by attaching its own mycelia (i.e. roots) to the roots of the host plant, and the plant supplies the fungus with carbon through its mycelia.

Exemplary genera of ectomycorrhizal fungus contemplated by the present invention include but are not limited to *Tuber, Cantharellus, Boletus, Tricholoma, Hydnum, Lepista, Amanita, Russula, Morchella, Rhizopogon, Craterellus, Lactarius, Polyozellus, Chroogomphus, Laccaria, Albatrellus, Suillus, Cortinarius, Gomphus, Entoloma, Lyophyllum, Leccinum* and *Inocybe*. Other genus of ectomycorrihizal fungi are described in Rinaldi et al., Fungal Diversity 33: 1-45, the contents of which are incorporated herein by reference.

According to a particular embodiment, the fruiting body of the ectomycorrhizal fungus is edible.

In the present invention, the term "edible" means safe or fit to be eaten by a human being.

Particular species of edible ectomycorrhizal fungii are those from the *Tuber* genus including, but are not limited to *Tuber melanosporum, Tuber magnatum, Tuber borchii, Tuber magnatum pico, Tuber aestivum, Tuber macrosporum, Tuber oregonense, Tuber gibbosum* and *Tuber lyonii*.

Other *Tuber* species contemplated by the present invention include those set forth in Table 1 herein below.

TABLE 1

| Name |
| --- |
| Tuber aestivum |
| Tuber affine |
| Tuber albidum |

TABLE 1-continued

| Name |
| --- |
| Tuber album |
| Tuber anniae |
| Tuber arenaria |
| Tuber argenteum |
| Tuber argentinum |
| Tuber asa-foetida |
| Tuber atrorubens |
| Tuber australe |
| Tuber bellisporum |
| Tuber belonei |
| Tuber berkeleyanum |
| Tuber bernardinii |
| Tuber besseyi |
| Tuber beyerlei |
| Tuber bisporum |
| Tuber bituminatum |
| Tuber blotii |
| Tuber bomiense |
| Tuber bonnetii |
| Tuber borchianum |
| Tuber borchii |
| Tuber brumale |
| Tuber californicum |
| Tuber canaliculatum |
| Tuber candidum |
| Tuber caroli |
| Tuber castaneum |
| Tuber castellanoi |
| Tuber castilloi |
| Tuber cervinum |
| Tuber cibarium |
| Tuber cinereum |
| Tuber cistophilum |
| Tuber citrin urn |
| Tuber clarei |
| Tuber croci |
| Tuber culinare |
| Tuber debaryanum |
| Tuber donnagotto |
| Tuber dryophilum |
| Tuber echinatum |
| Tuber eisenii |
| Tuber esculentum |
| Tuber excavatum |
| Tuber exiguum |
| Tuber ferrugineum |
| Tuber filamentosum |
| Tuber foetidum |
| Tuber fulgens |
| Tuber furfuraceum |
| Tuber fuscum |
| Tuber gallicum |
| Tuber gardneri |
| Tuber gibbosum |
| Tuber giganteum |
| Tuber gigantosporum |
| Tuber griseum |
| Tuber guevarai |
| Tuber gulonum |
| Tuber gulosorum |
| Tuber guzmanii |
| Tuber harknessii |
| Tuber hiemalbum |
| Tuber himalayense |
| Tuber hiromichii |
| Tuber huidongense |
| Tuber huizeanurn |
| Tuber indicum |
| Tuber intermedium |
| Tuber irradians |
| Tuber lacunosum |
| Tuber lapideum |
| Tuber latisporum |
| Tuber lauryi |
| Tuber lespiaultii |
| Tuber levissimurn |
| Tuber liaotongense |
| Tuber lignarium |

TABLE 1-continued

| Name |
|---|
| Tuber lijiangense |
| Tuber linsdalei |
| Tuber liui |
| Tuber longisporum |
| Tuber lucidum |
| Tuber lucidum |
| Tuber lutescens |
| Tuber luteum |
| Tuber lyoniae |
| Tuber macrosporum |
| Tuber maculatum |
| Tuber magnatum |
| Tuber malacodermum |
| Tuber malenconii |
| Tuber maresa |
| Tuber meandriformis |
| Tuber melanosporum |
| Tuber mesentericum |
| Tuber mexiusanum |
| Tuber michailowskianum |
| Tuber microspermum |
| Tuber microsphaerosporum |
| Tuber microspiculatum |
| Tuber microsporum |
| Tuber microverrucosum |
| Tuber minimum |
| Tuber miquihuanense |
| Tuber mixtum |
| Tuber monosporum |
| Tuber montagnei |
| Tuber montanum |
| Tuber monticola |
| Tuber moravicum |
| Tuber moretii |
| Tuber moschatum |
| Tuber mougeotii |
| Tuber multimaculatum |
| Tuber murinum |
| Tuber mutabile |
| Tuber nigrum |
| Tuber nitidum |
| Tuber niveum |
| Tuber nuciforme |
| Tuber obtextum |
| Tuber occidentale |
| Tuber oligosperm urn |
| Tuber oligosporum |
| Tuber olivaceum |
| Tuber oregonense |
| Tuber pacific urn |
| Tuber pallidum |
| Tuber panniferum |
| Tuber panzhihuanense |
| Tuber phlebodermum |
| Tuber piperatum |
| Tuber polyspermum |
| Tuber pseudoexcavatum |
| Tuber pseudohimalayense |
| Tuber puberulum |
| Tuber queletianum |
| Tuber quercicola |
| Tuber rapaeodorum |
| Tuber regianum |
| Tuber regimontanum |
| Tuber renati |
| Tuber requienii |
| Tuber rhenanum |
| Tuber rufum |
| Tuber radium |
| Tuber scleroneuron |
| Tuber scruposum |
| Tuber separans |
| Tuber shearii |
| Tuber sinense |
| Tuber sinoaestivum |
| Tuber sinoalbidum |
| Tuber sinoexcavatum |
| Tuber sinuosum |
| Tuber solidum |
| Tuber sphaerospermurn |
| Tuber sphaerosporum |
| Tuber spinoreticulatum |
| Tuber suecicum |
| Tuber taiyuanense |
| Tuber texense |
| Tuber umbilicatum |
| Tuber uncinatum |
| Tuber unicolor |
| Tuber vacini |
| Tuber venturii |
| Tuber verii |
| Tuber virens |
| Tuber virens |
| Tuber walkeri |
| Tuber whetstonense |
| Tuber xizangense |
| Tuber zeylanieum |
| Tuber zhongdianense |

As used herein the term "tree" refers to living woody perennial plants including bushes, shrubs, and large trees. The trees of this aspect of the present invention are preferably taller than 1 meter, and even preferably taller than 1.5 meters.

In one embodiment, the tree is one which has a primary root system known to harbor ectomycorrhizal fungal species. The term encompasses both deciduous and coniferous trees.

According to one embodiment, the tree is a mature tree.

According to another embodiment, the tree is a sapling.

The trees of this aspect of the present invention may be in a forest or a plantation. The forest may be a natural forest or a man-made forest. In one embodiment, the forest or plantation comprises heterogeneous species of trees. In another embodiment, the forest or plantation comprises no more than 10 species of trees, no more than 5 species of trees, no more than three species of trees, no more than two species of trees or a single species of trees.

The forest or plantation may comprise between 10-100,00 trees, 10-1000 trees, for example at least 10 trees, at least 20 trees, at least 50 trees, at least 100 trees, at least 200 trees, at least 500 trees.

Preferably at least 1% of the trees of the forest/plantation are used to cultivate the ectomycorrhizal fungi, at least 2% of the trees of the forest/plantation are used to cultivate the ectomycorrhizal fungi, at least 3% of the trees of the forest/plantation are used to cultivate the ectomycorrhizal fungi, at least 4% of the trees of the forest/plantation are used to cultivate the ectomycorrhizal fungi, at least 5% of the trees of the forest/plantation are used to cultivate the ectomycorrhizal fungi, at least 10% of the trees of the forest/plantation are used to cultivate the ectomycorrhizal fungi, at least 15% of the trees of the forest/plantation are used to cultivate the ectomycorrhizal fungi, at least 20% of the trees of the forest/plantation are used to cultivate the ectomycorrhizal fungi, at least 30% of the trees of the forest/plantation are used to cultivate the ectomycorrhizal fungi, at least 40% of the trees of the forest/plantation are used to cultivate the ectomycorrhizal fungi, at least 50% of the trees of the forest/plantation are used to cultivate the ectomycorrhizal fungi.

According to a particular embodiment, the tree is from the Fagaceae, Betulaceae and Juglandaceae families within the Fagales Order that include many common north temperate trees with varying number of species, some of which are important nut producing trees: oaks (*Quercus*), chestnuts (*Castanea*) and beeches (*Fagu*) in the Fagaceae Family; birches (*Betula*), alders (*Alnus*), hornbeams (*Carpinus*) and hazels (*Corylus*) in the Betulaceae Family; and walnuts (*Juglans*) and hickories (*Carya*) in the Juglandaceae Family. Additional flowering tree hosts contemplated by the present inventors are from the Salicaceae and Malvaceae families. They include willows (*Salix*) and poplars (*Populus*) in the Salicaceae Family, maples (*Acer*) in the Sapindaceae Family and lindens (*Tilia*) in the Malvaceae Family. Related to the Malvaceae is the Cistaceae Family of shrubs including sunroses (*Helianthemum*) and rockroses (*Cistus*), which are also contemplated. Conifers contemplated by the present inventors include pines (*Pinus*), firs (*Abies*), spruces (*Picea*), larches (*Larix*), and douglas fir (*Pseudotsuga*) in the Pinaceae Family and junipers (*Juniperus*) in the Cupressaceae Family.

In one embodiment, the tree is an oak, pine or douglas fir.

The term "root" is used herein to describe the non-leaf, non-node-bearing part of a plant.

The phrase "adventitious root" as used herein, refers to a root that arises from any point other than the radical or the root axis. The adventitious root of this aspect of the present invention is non-terrestrial (i.e. not planted in the ground in which the primary roots are planted), and at least a portion thereof is aerial. In addition, the adventitious root of this aspect of the present invention is connected to the tree.

In one embodiment, the adventitious roots emerge from the trunk of the tree.

Typical lengths of the adventitious roots of the present invention are between 3 cm-3 meters.

The adventitious roots may protrude from at least one, two, three, four, five, ten, 15, 20, 25 or 30 separate positions from a single tree. In a particular embodiment, the positions form a pattern such as a spiral pattern or a concentric circle around the tree. The number of adventitious roots typically depends on the size of the tree and the ability of the tree to produce the roots.

Methods of generating adventitious roots from trees are known in the art and include for example air layering techniques and soil layering techniques.

In air layering, a target region of a branch is wounded and surrounded in a moisture-retaining wrapper, such as, but not limited to, sphagnum moss, which is further surrounded in a moisture barrier, such as, but not limited to, a polyethylene film. When sufficient roots have grown from the wound, the wrapper is removed and the novel root cluster is planted in soil. This soil is preferably one encourages growth of the adventitious root (e.g. a nutrient rich soil). Preferably, this soil is devoid of Ectomycorrhizal inoculant.

In soil layering, a target region of a branch is wounded and placed in soil or soil replacement to induce root growth in situ. Also this soil is preferably one which encourages growth of the adventitious root and devoid of Ectomycorrhizal inoculant.

Figure 1A:
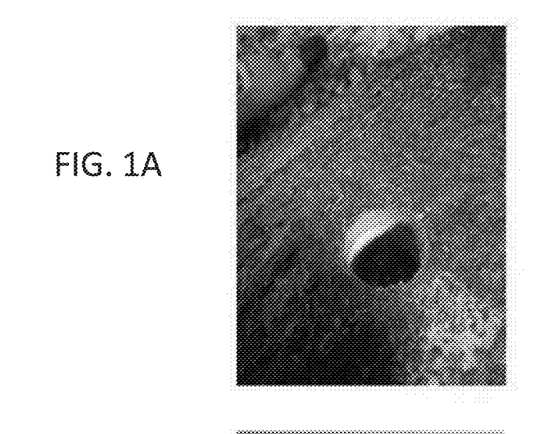

Thus, in one embodiment, a wound is made on a branch or on the trunk of the tree so as to induce generation of the adventitious root. This may be effected on multiple locations of a single tree as further described above. An exemplary wound is illustrated in FIG. 1A. The wound is typically 1 mm to 100 mm in size. The root may be encouraged to grow by applying plant hormones and plant growth regulators which promote generation of the roots. Optionally antibiotics may be added to the wound as well.

Examples of plant hormones and plant growth regulators include, but are not limited to Abscisic acid, auxins, cytokinins, ethylene, gibberllins, Brassinosteroids, Salicylic acid, Jasmonates, Plant peptide hormones, Polyamines, nitric oxide, strigolactones, Karrikins, nitric oxide, strigolactones and karrikins.

According to a particular embodiment, the rooting hormone or growth regulator is abscisic acid (ABA), 1-Naphthalene acetic acid (NAA) and/or 1-Naphthaleneacetamide.

Figure 2A:
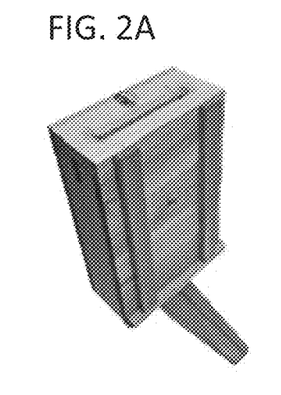
FIGS. 2A-B are images of a container according to embodiments of the present invention. The container has a removable cover protecting a glass window for monitoring the box interior.
Figure 2B:
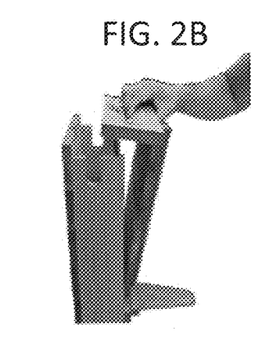
Figure 2C:
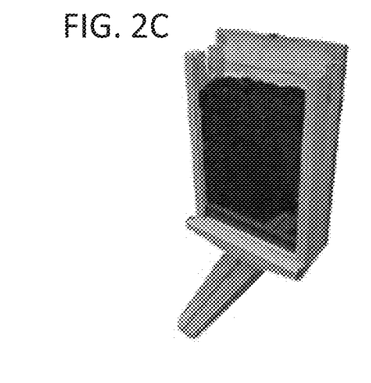
FIG. 2C is an image of the container filled with soil.
Figure 2D:
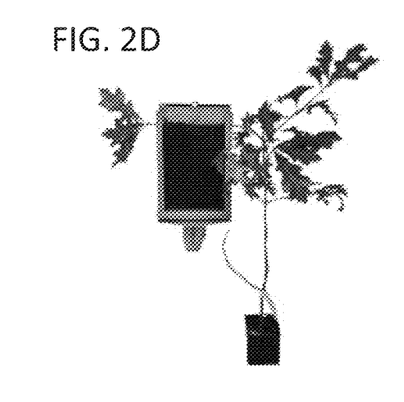
FIG. 2D is an image of the container filled with soil, wherein the roots of a young sapling have been passed through in order to generate adventitious roots.

As mentioned, in another embodiment, adventitious roots are generated by soil layering—passing a branch/stem of a sapling into a container comprising soil—see for example FIG. 2D. Preferably, the sapling is no older than 3 years. Stems that are slow to root may be treated with a plant hormone and/or subjected to wounding as described herein above.

Once the adventitious root has developed to a sufficient extent, the nutrient soil in which it is planted is removed (e.g. rinsed from the root).

For inoculation, the adventitious root is contacted with an ectomycorrhizal fungus. Preferably, the adventitious roots is planted in a soil that encourages growth of the fungus (e.g. a nutrient poor soil) prior to inoculation, as further described herein below. The Ectomycorrhizal inoculant may be added via a watering system, or added directly into the inoculation soil.

Methods of producing ectomycorrhizal fungi inoculants are known in the art—see for example Rossi et al., Food Technol Biotechnol 45:277-286, the contents of which are incorporated herein by reference. U.S. Pat. No. 5,178,642 discloses a process for production of inocula for herbaceous plants. U.S. Pat. No. 4,327,181 discloses a liquid culture of selected fungi for broadcast over forest soil.

It will be appreciated that inoculation of non-planted adventitious roots is also contemplated. In this case, ectomycorrhizal inoculants (e.g. in a powder form or a gel form) may be contacted (e.g. sprinkled) onto exposed roots.

In one embodiment, the ectomycorrhizal inoculant may comprise a purified inoculum of a single ectomycorrhizal fungus genus or from a plurality of ectomycorrhizal fungal genii. In another embodiment, the inoculum may comprise spores, e.g. those present in the fruiting bodies of the fungus. In yet another embodiment, the ectomycorrhizal inoculant is derived from earth/soil surrounding a tree which is known to be infected with an ectomycorrhizal fungus. In still another embodiment, the ectomycorrhizal inoculant comprises differentiated mycelium hyphae, for example those found in stem butts. Thus, the ectomycorrhizal inoculants may comprise rhizomorphs. In another embodiment, the inoculum may comprise root samples.

Following inoculating, the ectomycorrhizal fungus is grown on the adventitious root of the tree. As mentioned, in order to grow, the soil in which the adventitious root is planted is one which allows the symbiotic relationship of the ectomycorrhizal fungus with the adventitious root to develop.

The formation of ECM symbiosis can be significantly improved by selected soil and mycorhizosphere bacteria (*Bacillus, Burkolderia, Paenibacillus, Pseudomonas, Streptomyces*) named "mycorrhiza helper bacteria" (MHB). These are further described in Savoie et al., Appl Microbial Biotechnol (2011) 89:971-979, the contents of which is incorporated herein by reference.

U.S. Pat. No. 4,749,402 describes a method for enhancing the development of mycorrhizal fungi in the root system of a plant. Particularly, this invention relates to a nutrient composition adapted for foliar fertilization of a plant to enhance the development of mycorrhiza on the root system. This composition comprises magnesium, boron, nitrogen, ammonium sulfate, phosphorous, potassium and sulfur and has a pH ranging from 5.5 to 6.5.

In one embodiment, the soil is devoid of at least one essential element, nutrient or mineral such that the adventitious root requires and or is dependent on the propagation of the ectomycorrhizal fungus therein. Thus, for example the soil may be devoid of at least one of the following elements: nitrogen, potassium, calcium, phosphorous, sulfur, magnesium or iron.

In order to monitor whether a successful mycorrhizal relationship has been established a root sample may be taken and the expression level of ectomycorrhizal a fungus specific polypeptide may be determined. Examples of such proteins include but are not limited to Mycorrhiza-induced small secreted protein-7 (MiSSP7). Methods of analyzing expression levels of proteins are known in the art and include for example PCR, RT-PCR, Immunohistochemistry, Western Blot analysis and Northern blot analysis.

Other methods for determining establishment of mycorrhizal symbiosis are described in the literature—see for example, Seddas-Dozolme P M., Methods Mol Biol. 2010; 638:137-52. doi: 10.1007/978-1-60761-611-5_10, and Vierheilig et al., Physiologia Plantarum 125: 393-404, 2005 and US Patent No. 20050132431, the entire contents of which are incorporated herein by reference.

The soil which is in contact with the adventitious root is planted for inoculation and subsequent cultivation may be treated such that it is devoid of other bacterial or fungal contaminants. The soil may comprise additional agents which promote propagation of the ectomycorrhizal fungus, including but not limited to yeast extract, glucose, fertilizers, pesticides and admixtures of biochar.

Preferably, the soil into which the adventitious root is planted is held in a container.

The term "container" is used herein to describe a restricted space which comprises an aperture or portal of dimension suitable to allow entry of the adventitious root.

Thus according to another aspect of the present invention there is provided a container for cultivating an ectomycorrhizal fungus on a tree, the container comprising means for hanging the container on a trunk of the tree and at least one aperture for entry of a non-terrestrial adventitious root of the tree, the at least one aperture being positioned such that the non-terrestrial adventitious root is not exposed to light when cultivated in the container which is filled with soil.

Figure 1B:
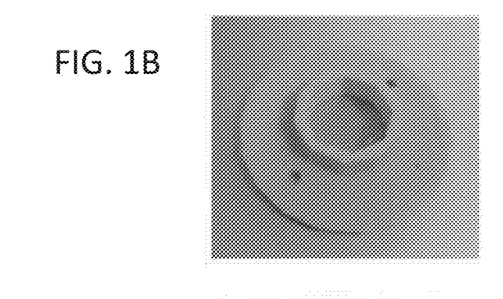
Figure 1C:
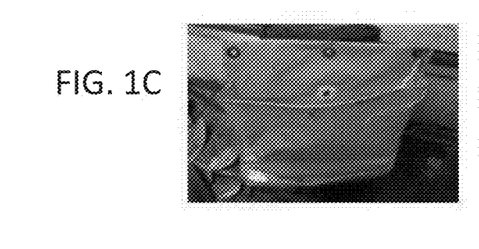
Figure 1D:
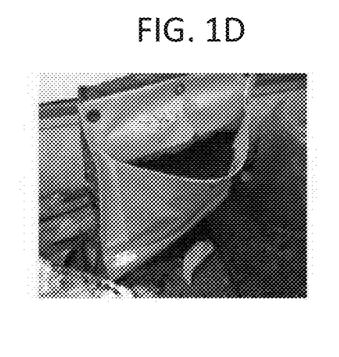

Exemplary containers suitable for use according to this aspect of the present invention are presented in FIGS. 1C, 2A and 2C.

Thus, the container may be in the shape of a box, a bag or an envelope.

The container may comprise rigid walls or flexible walls.

The container may be of any shape, including round, square and or rectangle. Contemplated sizes of the containers are 50 cc-40,000 cc.

The aperture which provides a conduit for non-terrestrial adventitious root to enter the container is positioned such that no part of the non-adventitious root is exposed to light when cultivated in the container which is filled with soil. In one embodiment, the aperture is no more than 5 cm from the bottom surface of the container, no more than 10 cm from the bottom surface of the container, no more than 15 cm from the bottom of the container. In order to avoid the non-adventitious root from being exposed to light, the aperture may be placed directly over the wound of the tree, such that on emerging from the tree, the adventitious root grows directly into the container which is filled with soil.

In one embodiment, the container of this aspect of the present invention is closed on all sides and the only opening to the exterior in the container is the aperture. Preferably, for this embodiment, the container is fabricated from a porous material such that the soil within can be watered and also drained.

In one embodiment, the container comprises a hook or a handle such that it can be hung from the tree. Alternatively or additionally, the container may hang from the tree from a grommet which is fitted into the aperture—see for example FIGS. 1B-C.

The container is typically fabricated from a material that does not decompose or biodegrade for at least the length of time required for the ectomycorrhizal fungus to grow.

In one embodiment, the material is porous, allowing the flow of water. In another embodiment, the material is non-porous, but comprises a least one aperture allowing water to escape and/or aeration (e.g. located at the bottom surface).

Preferably, the container is fabricated from a material that is not permeable to light.

In one embodiment, the container is fabricated from plastic, wood, a textile (e.g. geotextile), a ceramic, a paper product such as cardboard, or a plant derived material such as wicker or coir. The container may be fabricated from a biodegradable or non-biodegradable material. Thus, the present inventor contemplates fabricating the container from a rigid material or a non-rigid (flexible) material.

In one embodiment, at least a portion of the container is permeable to light so as to allow monitoring of the growth of the ectomycorrhizal fungus. This portion is typically fabricated from a transparent material such as glass, plastic or Perspex. Preferably, this portion is located along one vertical wall of the container at a position where it is possible to analyze growth of the fungus—see for example FIGS. 2C-D.

Figure 6A:
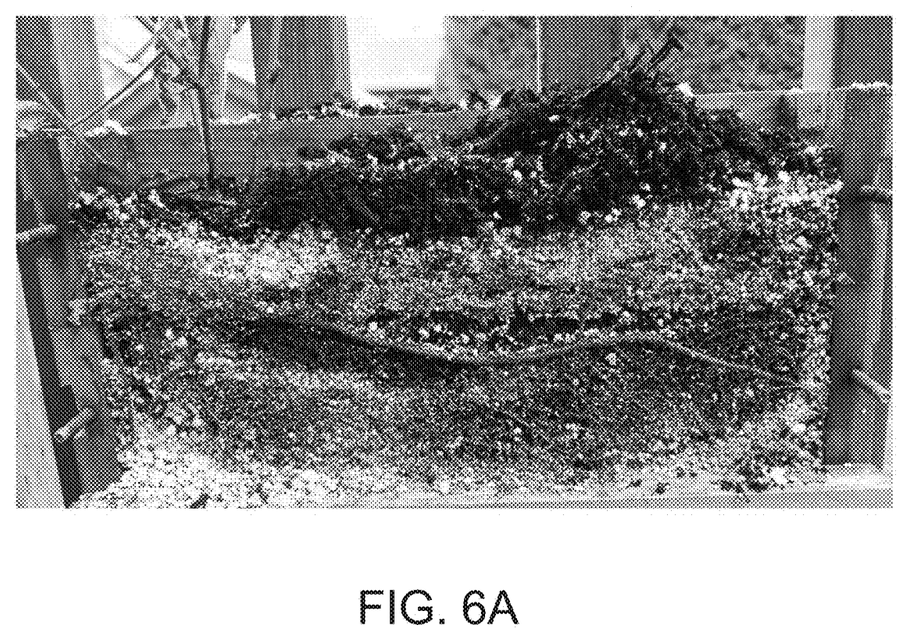
FIGS. 6A-B are photographs of containers showing growth of non-terrestrial adventitious roots within the soil. In 6A, the root is seen growing nearly horizontally from the branch (branch at upper left), with oblique and nearly vertical rootlets extending obliquely and nearly vertically. In 6B, the root is seen growing nearly vertically with respect to the branch (branch at upper right).
Figure 6B:
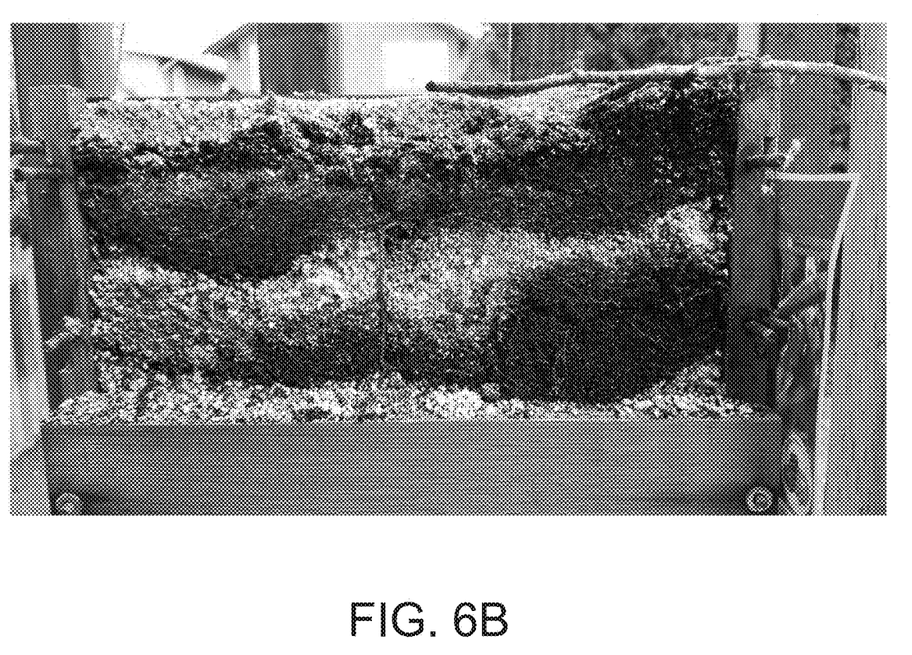

In another embodiment, this portion is located on the bottom surface of the container. The light permeable portion of the container may be covered by a removable cover which is impermeable to light so that when the light permeable portion of the container is covered, light does not penetrate the container, but when the light permeable portion of the container is uncovered, light does penetrate the container. The removable cover may be fabricated with the same material as the material used to fabricate the other walls of the container or from a different material to the material used to fabricate the other walls of the container. Thus, for example, the present invention contemplates the container being a wooden box wherein at least a portion of one wall of the container is made from glass (see for example FIG. 2C). The exterior of the glass may be covered by a wooden door, or a flap (e.g. made from plastic). FIGS. 6A and 6B each show a non-limiting example of the claimed container, with the front portion removed to reveal growth of the non-terrestrial adventitious root from a branch of the tree.

Preferably at least 25%, of the container is filled with soil, at least 50% of the container is filled with soil, or even at least 75% of the container is filled with soil.

The container which holds the adventitious root and the fungus of the present invention may be attached physically to the tree. In one embodiment, the container is attached at least 0.5 meters, or at least 1 meter above the ground which comprises the primary roots of the tree. Preferably, the container is attached such that the side of the container which comprises the aperture is flush with the tree. In one embodiment, the side of the container which is against the tree is curved such that it fits the shape of the tree.

As mentioned herein above, it is possible to generate more than one adventitious root from a tree. Therefore, the present inventors contemplate trees having a plurality of adventitious roots, wherein at least two of the plurality of adventitious roots are planted in separate containers. Thus, a single tree can have at one, two, three, four, five, six, seven, eight, nine, ten or more containers attached thereto, each comprising adventitious roots originating from different positions from the tree.

According to one embodiment, the tree comprises a plurality of non-terrestrial adventitious roots wherein at least two of the non-terrestrial adventitious roots are planted in soil in separate containers.

According to another embodiment, the tree comprises a plurality of non-terrestrial adventitious roots wherein each of the plurality of the non-terrestrial adventitious roots are planted in soil in separate containers.

The containers of this aspect of the present invention may further comprise an artificial irrigation system. Contemplated irrigation systems include drip irrigation systems such as those described in 20150195997 or 20140305041, the contents of which are incorporated herein by reference. Alternatively, the containers may be irrigated via sprinkler irrigation or spraying.

The container of embodiments of the present invention may further comprise a monitoring device such that it is possible to visualize the fungus and/or the adventitious roots without allowing light to penetrate the container (rhizotron). Thus, for example, the container may comprise a transparent container that is immersed into the soil which contains a camera. More information on the use of rhizotrons may be found in the book Plant Roots: the hidden half, 4$^{th}$ edition, Capter 42: 42-1, 42-5, 42-6, 2012, the contents of which is incorporated herein by reference.

The ectomycorrhizal fungi may be grown (propagated) for any period of time according to the requirements of the user. For example, the ectomycorrhizal fungi may be grown for 1-20 years, 1-10 years, 5-10 days.

Figure 3A:
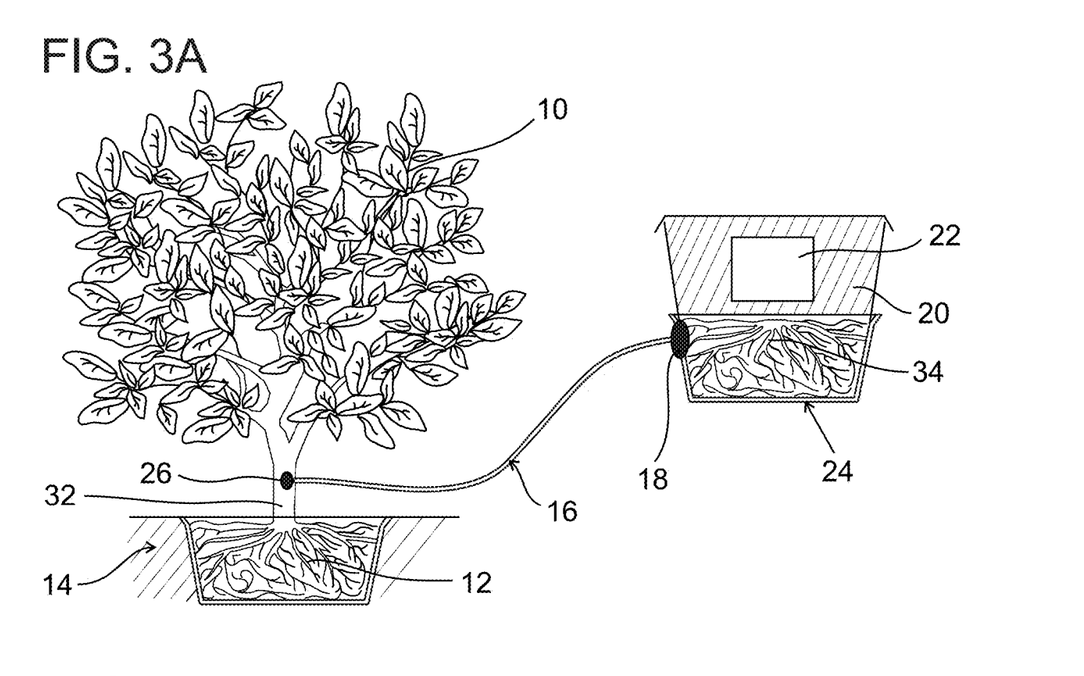
FIGS. 3A-B illustrate how ectomycorrhizal fungi may be cultivated on adventitious roots of trees according to embodiments of the present invention.

FIGS. 3A-5B further illustrate some of the embodiments described herein. FIG. 3A portrays a tree 10, having a trunk 32 and roots 12, which are planted in the ground 14. The trunk of the tree 32 comprises a wound 26 from which adventitious roots 16 protrude. The adventitious roots 16 are planted in a container 24 comprising soil 20. The adventitious roots 16 enter the container 24 via an aperture 18. The container 24 is light impermeable so as to mimic underground conditions which are required by the ectomycorrhizal fungi 34 to grow.

For illustration purpose only, the adventitious root 16 is shown here as being exposed to the light. However, for the present invention, the adventitious root 16 is not exposed to light conditions.

Figure 3B:
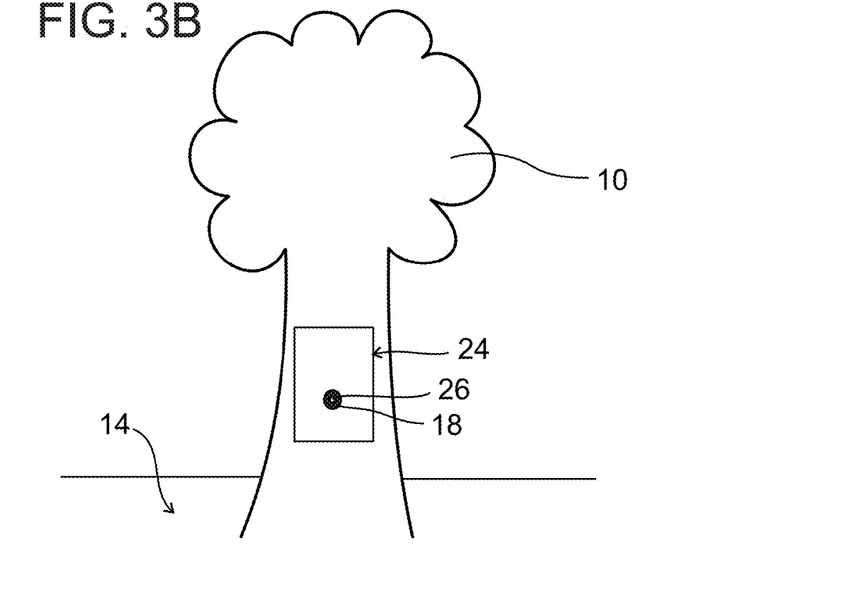

FIG. 3B illustrates the tree 10 with the container 24 attached thereto such that the adventitious root 16 emerging from the wound 26 grows directly from the tree 10 and into the container 24 without being exposed to light. In one embodiment, the container 24 is hung from the tree 10 by a hook 18 which fits into the wound 26.

Figure 4A:
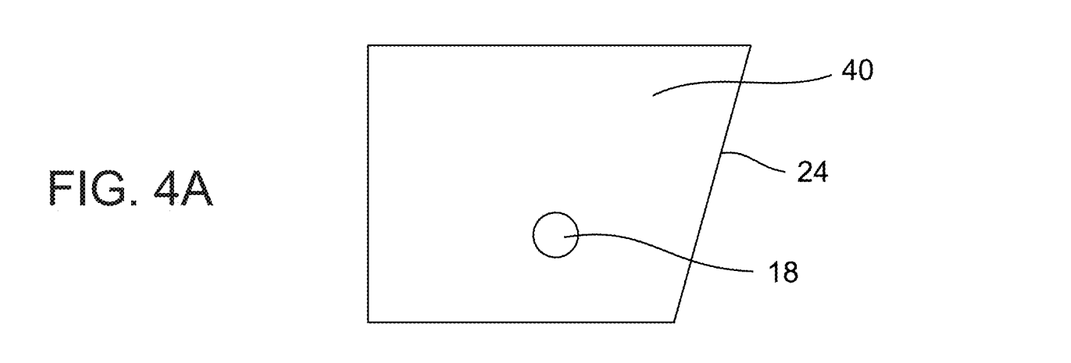
FIGS. 4A-C are different views of the container according to embodiments of the present invention.

FIG. 4A illustrates an embodiment of an external wall 40 of the container 24. In this embodiment, the external wall 40 comprises an aperture 18 through which to allow entry of adventitious roots of a tree. The external wall 40 is placed on the trunk 32 of the tree 10.

Figure 4B:
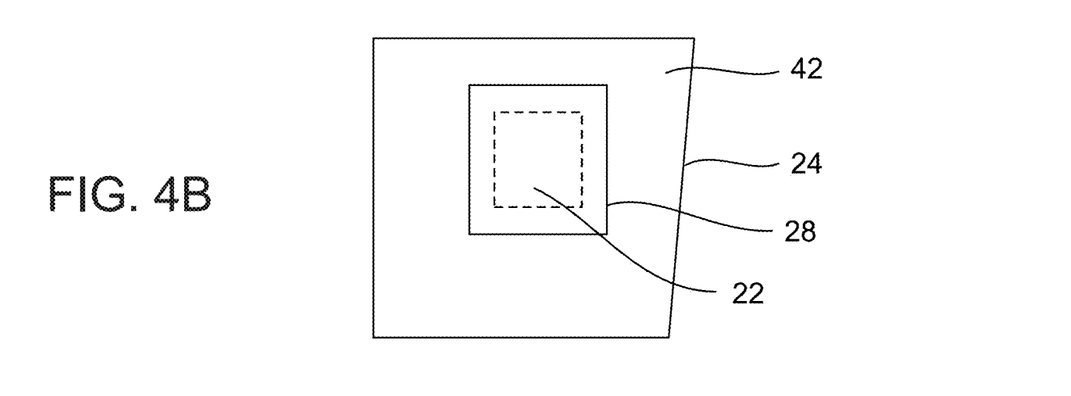

FIG. 4B illustrates an embodiment of a second external wall 40 of the container 24. In this embodiment, the external wall 40 comprises a cover 28 which may be removed to expose a light permeable portion 22 of the container. The cover 28 may be attached to the container by a hinge. Alternatively, the cover 28 may be a flap and lifted so as to expose the light permeable portion 22. In another embodiment, the cover 28 may be a sliding door. The light permeable portion 22 of the container is preferably at a position such that when uncovered, it is possible to see the adventitious roots 16 of the tree and preferably the infecting ectomycorrhizal fungi 34 and/or fruiting body 36 thereof. Preferably, the side of the container which comprises the aperture 18 is not the same side which comprises the cover 28.

Figure 4C:
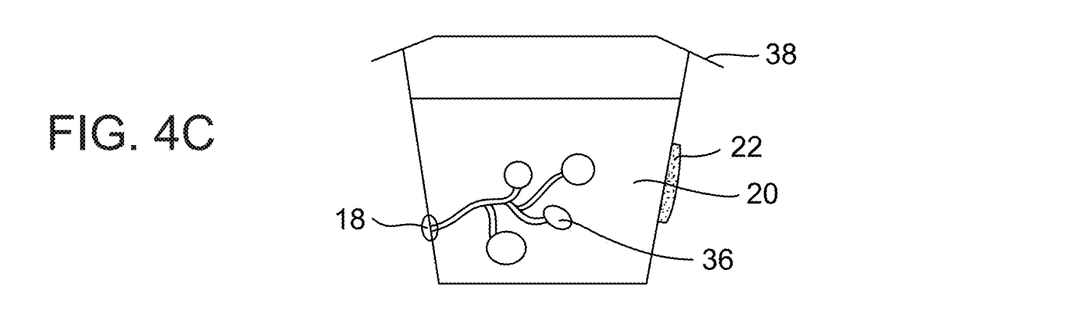

FIG. 4C is another view of the container 24, illustrating the growth of the ectomycorrhizal fungi 34 on the adventitious root 16. The root is covered in soil 20.

In one embodiment, the container 24 is covered with a light impermeable cover 38. In another embodiment, the container 24 does not comprise a cover. In this embodiment, the amount of soil is such that the adventitious roots and ectomycorrhizal fungi 34 grow in conditions that simulate underground growth and the fungi is not exposed to light.

Figure 5A:
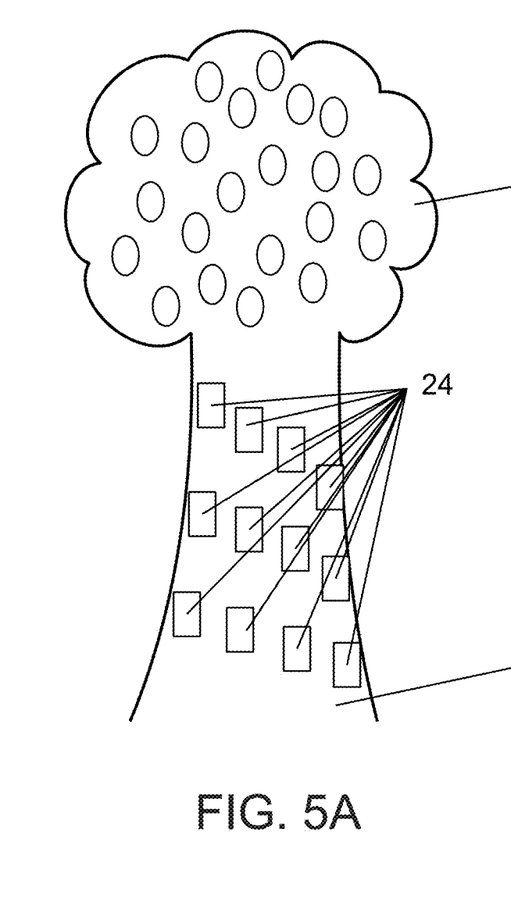
FIGS. 5A-B are views of trees to which the containers have been attached according to embodiments of the present invention.
Figure 5B:
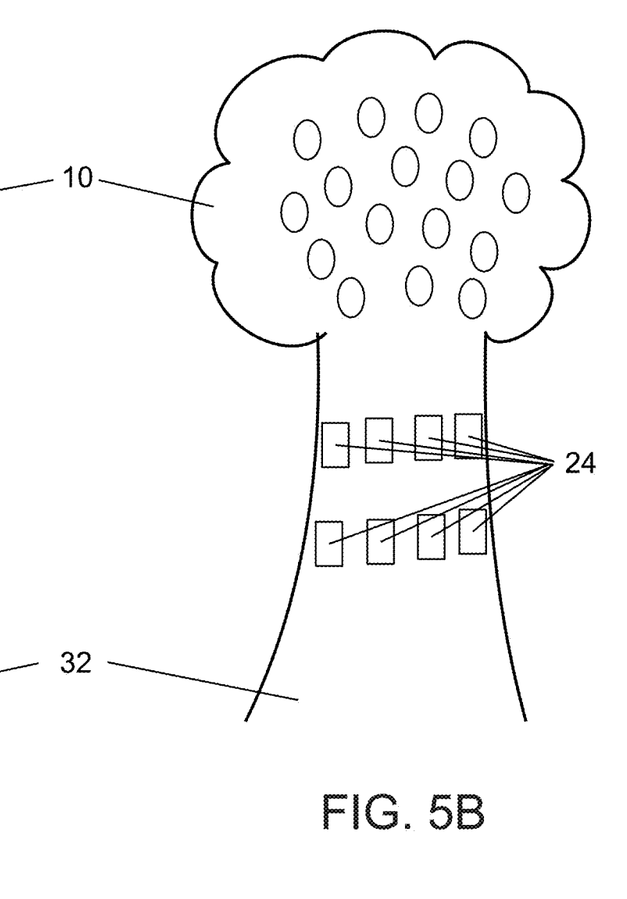

FIGS. 5A-5B illustrate trees 10 to which a plurality of containers 24 have been attached. The containers may be attached such that they form a pattern on the trunks 32 of the trees 10.

In one embodiment, the ectomycorrhizal fungi are grown until generation of a fruiting body. The fruiting body may be epigeous (above the ground) or hypogeous (under the ground).

Monitoring the growth of the ectomycorrhizal fungi may be effected by visualizing the ectomycorrhizal fungi via the portion of the container that is permeable to light. In one embodiment, the portion of the container that is permeable to light allows for visualization of epigeous fruiting bodies. In another embodiment, the portion of the container that is permeable to light allows for visualization of hypogeous fruiting bodies. In still another embodiment, the portion of the container that is permeable to light allows for visualization of both epigeious or hypogeous fruiting bodies.

Alternatively, monitoring the growth of the ectomycorrhizal fungi may be effected using a recording device, e.g. a camera, as described herein above.

Additional methods of monitoring the growth of the ectomycorrhizal fungi may be used such as monitoring the quantity of an ectomycorrhizal fungi specific proteins in the soil or on the root. A rapid molecular typing method for reliable detection of Asian black truffle species has also been developed to identify fruiting bodies and mycorrhizal infections (Mabru et al. 2001; Mycorrhiza, 11: 89-94). PCR (polymerase chain reaction) methods were devised for the detection of *Boletus edulis* and other species of *Boletus* and *Suillus* in foods (Moor et al. 2002; Eur. Food Res. Technol. 214: 340-345).

The system described herein can be used to analyze the effect of a particular agent on the growth of the ectomycorrhizal fungi. The agent may be added to the soil and the effect on the growth of the ectomycorrhizal fungi may be monitored over a particular length of time using the methods described herein above.

The fruit of the ectomycorrhizal fungi may be detected (even if the absence of monitoring) using rodents such as squirrels—see for example Sanjay Pyare and William S. Longland, Can. J. Zool. 79: 1007-1015 (2001), the contents of which are incorporated herein by reference.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the horticultural, chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of cultivating an ectomycorrhizal fungus on a tree, comprising growing the ectomycorrhizal fungus on at least one inoculated non-terrestrial adventitious root of the tree, thereby cultivating the ectomycorrhizal fungus on the tree, and wherein said growing said ectomycorrhizal fungus is effected in a container, wherein said ectomycorrhizal fungus is an edible ectomycorrhizal fungus of a genus selected from the group consisting of *Tuber, Cantharellus, Boletus, Tricholoma, Hydnum, Lepista, Amanita, Russula, Morchella, Rhizopogon, Craterellus, Lactarius, Polyozellus, Chroogomphus, Laccaria, Albatrellus, Suillus, Amanita, Cortinarius, Gomphus, Entoloma* and *Inocybe*, wherein said tree is selected from the group consisting of Hazel (*Corylus*), Oak (*Quercus*), Beech (*Fagu*), Fir (*Abies*), Poplar (*Populus*) and Birch (*Betula*) and wherein said non-terrestrial adventitious root is connected to the tree.

2. The method of claim 1, further comprising contacting said at least one non-terrestrial adventitious root of the tree with the ectomycorrhizal fungus under conditions suitable for inoculation of said at least one adventitious root by the ectomycorrhizal fungus prior to said growing.

3. The method of claim 1, wherein said tree is at least one meter high.

4. The method of claim 1, wherein said ectomycorrhizal fungus is an edible ectomycorrhizal fungus of a genus selected from the group consisting of *Tuber, Cantharellus, Boletus, Tricholoma, Hydnum, Lepista, Amanita, Russula, Morchella* and *Rhizopogon*.

5. The method of claim 1, wherein said tree is a Haxel (*Corylus*) or an Oak (*Quercus*).

6. The method of claim 2, wherein said contacting is effected by:
(a) planting said non-terrestrial adventitious root in soil adapted for growth of said ectomycorrhizal fungus which comprise an inoculum of said ectomycorrhizal fungus, or
(b) planting said non-terrestrial adventitious root in soil adapted for growth of said ectomycorrhizal fungus and inoculating said soil with said ectomycorrhizal fungus.

7. The method of claim 6, wherein said soil naturally comprises rhizomorphs of ectomycorrhizal fungus.

8. The method of claim 1, wherein at least a portion of the container is permeable to light so as to allow monitoring of the growth of the ectomycorrhizal fungus and, optionally, wherein said permeable portion of said container is covered by a removable cover, said removable cover being impermeable to light so as to block light permeation in the absence of said monitoring.

9. The method of claim 1, wherein said container comprises a rhizotron.

10. The method of claim 1, wherein said container is fixed to the tree.

11. The method of claim 2, wherein said growing is effected until generation of a fruiting body from said ectomycorrhizal fungus.

12. A tree comprising at least one non-terrestrial adventitious root, said root being inoculated by an ectomycorrhizal fungus, wherein said non-terrestrial adventitious root is planted in soil in a container, wherein said ectomycorrhizal fungus is an edible ectomycorrhizal fungus of a genus selected from the group consisting of *Tuber, Cantharellus, Boletus, Tricholoma, Hydnum, Lepista, Amanita, Russula, Morchella, Rhizopogon, Craterellus, Lactarius, Polyozellus, Chroogomphus, Laccaria, Albatrellus, Suillus, Amanita, Cortinarius, Gomphus, Entoloma* and *Inocybe*, wherein said tree is selected from the group consisting of Hazel (*Corylus*), Oak (*Quercus*), Beech (*Fagu*), Fir (*Abies*), Poplar (*Populus*) and Birch (*Betula*) and wherein said non-terrestrial adventitious root is connected to the tree.

13. The tree of claim 12, wherein the tree is at least one meter high.

14. The tree of claim 12, comprising a plurality of non-terrestrial adventitious roots wherein at least two of said non-terrestrial adventitious roots are planted in soil in separate containers.

15. The tree of claim 12, wherein at least a portion of the container is permeable to light so as to allow monitoring of the growth of the ectomycorrhizal fungus and optionally wherein said permeable portion of said container is covered by a removable cover, said removable cover being impermeable to light so as to block light permeation in the absence of said monitoring.

\* \* \* \* \*